US009636099B2

(12) United States Patent
Rodrigues, Jr.

(10) Patent No.: US 9,636,099 B2
(45) Date of Patent: *May 2, 2017

(54) SURGICAL ACCESS SYSTEM INCLUDING SURGICAL PORTAL APPARATUS AND ADHESIVE PATCH

(71) Applicant: Covidien LP, Mansfield, MA (US)

(72) Inventor: Anibal Rodrigues, Jr., Milford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/147,042

(22) Filed: May 5, 2016

(65) Prior Publication Data

US 2016/0242759 A1    Aug. 25, 2016

Related U.S. Application Data

(63) Continuation of application No. 14/235,099, filed as application No. PCT/US2012/048913 on Jul. 31, 2012, now Pat. No. 9,351,760.
(Continued)

(51) Int. Cl.
*A61B 17/02* (2006.01)
*A61M 39/02* (2006.01)
(Continued)

(52) U.S. Cl.
CPC ...... *A61B 17/0218* (2013.01); *A61B 17/3423* (2013.01); *A61M 39/0247* (2013.01);
(Continued)

(58) Field of Classification Search
CPC ............ A61B 17/3423; A61B 17/0293; A61B 2017/00951; A61B 2017/3445;
(Continued)

(56) References Cited

U.S. PATENT DOCUMENTS 4,899,762 A    2/1990 Muller
6,124,521 A    9/2000 Roberts
(Continued)

FOREIGN PATENT DOCUMENTS

CN    101401742 A    4/2009
EP    0206646 A2    12/1986

OTHER PUBLICATIONS

European Seach Report EP 12 82 4273 dated Jan. 19, 2015.
(Continued)

*Primary Examiner* — Eduardo C Robert
*Assistant Examiner* — David C Comstock

(57) ABSTRACT

The present disclosure relates to surgical access systems and methods of using the same to access a surgical site during a surgical procedure. The surgical access system includes a portal member and a patch. The portal member includes at least one longitudinal port for passage of a surgical object. The portal member is formed from a compressible material and is adapted to transition from a first expanded condition to a second compressed condition such that an outer surface of the portal member is adapted for a substantial sealing relation with an opening in tissue upon insertion of the portal member therethrough. The patch includes a non-porous substrate having a tissue facing surface including an adhesive for positioning over the opening in the tissue and sealing a surface thereof. The patch is adapted for sealed reception of the portal member.

16 Claims, 2 Drawing Sheets

Related U.S. Application Data

(60) Provisional application No. 61/522,790, filed on Aug. 12, 2011.

(51) Int. Cl.
*A61B 17/34* (2006.01)
*A61B 17/00* (2006.01)
*A61B 46/20* (2016.01)

(52) U.S. Cl.
CPC . *A61B 17/0293* (2013.01); *A61B 2017/00951* (2013.01); *A61B 2017/00955* (2013.01); *A61B 2017/0225* (2013.01); *A61B 2017/3419* (2013.01); *A61B 2017/3445* (2013.01); *A61B 2017/3492* (2013.01); *A61B 2046/205* (2016.02); *A61M 2039/0279* (2013.01)

(58) Field of Classification Search
CPC .... A61B 2017/3492; A61B 2017/3419; A61B 2019/085; A61M 2039/0279
USPC ........ 600/201, 206, 208, 227; 128/849, 850, 128/856
See application file for complete search history.

(56) References Cited

U.S. PATENT DOCUMENTS

| | | |
|---|---|---|
| 6,286,511 B1 * | 9/2001 | Levitt ................ A61B 46/00 128/849 |
| 6,290,708 B1 | 9/2001 | Kugel et al. |
| 6,382,211 B1 | 5/2002 | Crook |
| 6,855,135 B2 | 2/2005 | Lockwood et al. |
| 9,351,760 B2 * | 5/2016 | Rodrigues, Jr. ... A61M 39/0247 |
| 2005/0070858 A1 | 3/2005 | Lockwood et al. |
| 2009/0093752 A1 * | 4/2009 | Richard ............. A61B 17/3423 604/24 |
| 2009/0240343 A1 | 9/2009 | Adams |
| 2010/0036197 A1 * | 2/2010 | Mesallum .......... A61B 17/0218 600/104 |
| 2010/0298646 A1 | 11/2010 | Stellon et al. |

OTHER PUBLICATIONS

International Search Report for PCT/US2012/048913 date of completion is Feb. 13, 2013 (5 pages).
Chinese Office Action dated Oct. 10, 2015, issued in Chinese Application No. 201280039514.
Chinese Office Action dated May 24, 2016, issued in Chinese Application No. 201280039514.7.

* cited by examiner

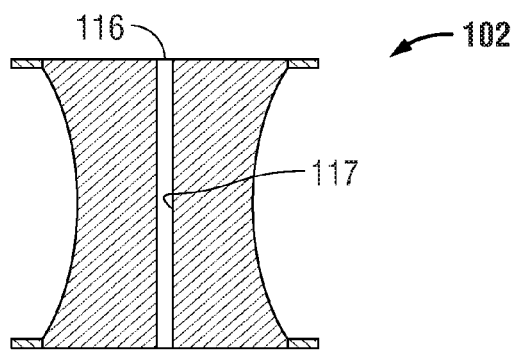
FIG. 2
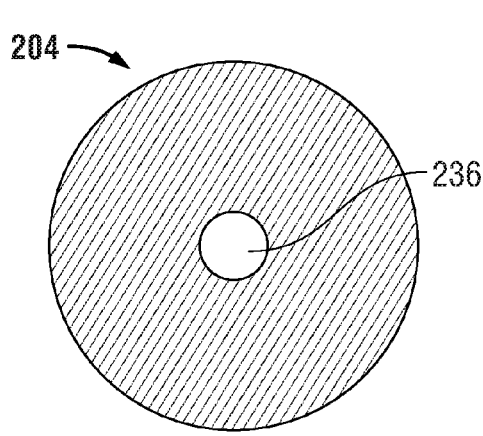
FIG. 3A
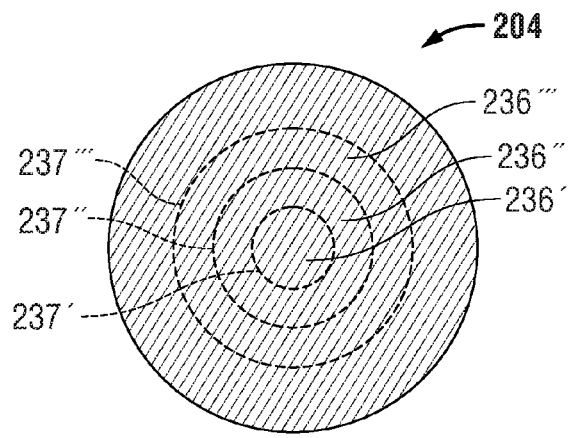
FIG. 3B
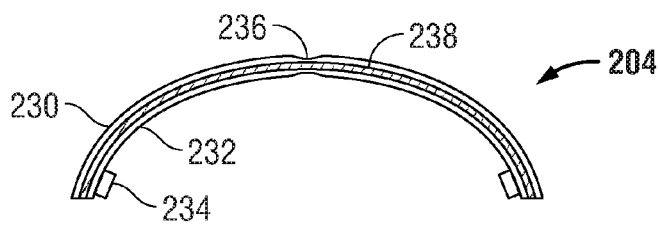
FIG. 4A
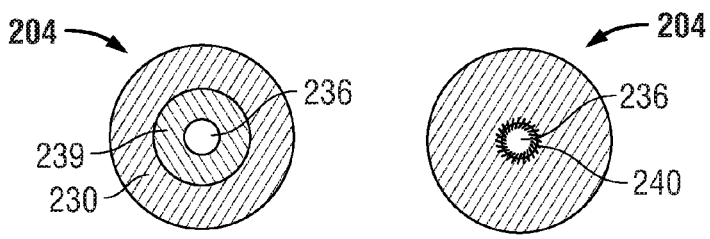
FIG. 4B
FIG. 4C

SURGICAL ACCESS SYSTEM INCLUDING SURGICAL PORTAL APPARATUS AND ADHESIVE PATCH

CROSS-REFERENCE TO RELATED APPLICATIONS

This application is a Continuation of U.S. patent application Ser. No. 14/235,099 filed Jan. 27, 2014, which is a National Stage Application of PCT/US12/48913 under 35 USC §371(a), which claims priority of U.S. Provisional Patent Application Ser. No. 61/522,790 filed Aug. 12, 2011, and the disclosures of each of the above-identified applications are hereby incorporated by reference in their entirety.

BACKGROUND

Technical Field

The present disclosure relates generally to a surgical access system for use in a surgical procedure, and more particularly, to a surgical access system including a surgical portal apparatus and an adhesive patch for forming a fluid tight seal with both tissue and one or more surgical objects positioned therethrough.

Background of Related Art

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

During a typical minimally invasive procedure, surgical objects, such as surgical access devices, e.g., trocar and cannula assemblies, or endoscopes, are inserted into the patient's body through the incision in tissue. In general, prior to the introduction of the surgical object into the patient's body, insufflation gases are used to enlarge the area surrounding the target surgical site to create a larger, more accessible work area. Accordingly, the maintenance of a substantially fluid-tight seal is desirable so as to prevent the escape of the insufflation gases and the deflation or collapse of the enlarged surgical site.

To this end, various surgical ports with valves and seals are used during the course of minimally invasive procedures and are widely known in the art. The small incisions, however, are typically enlarged for specimen removal from the patient's body. The enlarged opening prohibits continued use of the surgical port therethrough as the opening has become too large to maintain a fluid-tight seal with the surgical port. Additional incisions may be required for continued access of the surgical site with a surgical port.

A continuing need exists for a surgical access system that can facilitate the accessibility of an underlying tissue site with relative ease and with minor inconvenience for a clinician. It would be advantageous to provide a surgical access system that would allow for continued use, or re-use, of a surgical port after an incision is enlarged while maintaining a fluid tight seal with the enlarged incision.

SUMMARY

The present disclosure relates to surgical access systems and methods of using the same during a surgical procedure. The surgical access system includes a portal member and a patch. The portal member includes at least one longitudinal port for passage of a surgical object. The portal member is formed from a compressible material and is adapted to transition from a first expanded condition to a second compressed condition such that an outer surface is adapted for a substantial sealing relation with an opening in tissue upon insertion of the portal member therethrough. The patch includes a non-porous substrate having a tissue facing surface including an adhesive for positioning over the opening in the tissue and sealing a surface thereof. The patch is adapted for sealed reception of the portal member.

In accordance with one embodiment of the present disclosure, to access a surgical site, a patch including a non-porous substrate having a tissue facing surface including an adhesive is placed over an opening in tissue and seals a surface thereof. A portal member is then positioned through an aperture in the patch. The portal member includes at least one longitudinal port for passage of a surgical object. The portal member is formed from a compressible material and is adapted to transition from a first expanded condition to a second compressed condition such that an outer surface is adapted for a substantial sealing relation with the aperture of the patch and the opening in the tissue upon insertion of the portal member therethrough.

In accordance with another embodiment of the present disclosure, to access a surgical site, a portal member including at least one longitudinal port for passage of a surgical object is placed in an opening in tissue. The portal is formed from a compressible material and is adapted to transition from a first expanded condition to a second compressed condition such that an outer surface is adapted for a substantial sealing relation with the opening in the tissue upon insertion of the portal member therethrough. Surgical objects are placed through the at least one longitudinal port. The portal member is removed from the opening in the tissue and the opening of the tissue is enlarged. A patch including a non-porous substrate having a tissue facing surface including an adhesive is positioned over the enlarged opening in the tissue and seals a surface thereof. The portal member may then be placed through the patch in sealed relation therewith.

BRIEF DESCRIPTION OF THE DRAWINGS

Various embodiments of the present disclosure are described hereinbelow with reference to the drawings, wherein:

FIG. 2 is a cross-sectional view of the portal member of FIG. 1 taken along line 2-2 of FIG. 1 illustrating a longitudinally extending port of the seal anchor member;

FIG. 3A is a top view of a patch in accordance with another embodiment of the present disclosure;

FIG. 3B is a top view of a patch in accordance with yet another embodiment of the present disclosure;

FIG. 4A is a cross-sectional view of the patch of FIG. 3A in accordance with one embodiment of the present disclosure;

FIG. 4B is a top view of a patch in accordance with another embodiment of the present disclosure; and FIG. 4C is a top view of a patch in accordance with yet another embodiment of the present disclosure.

DETAILED DESCRIPTION OF EMBODIMENTS

Figure 1:
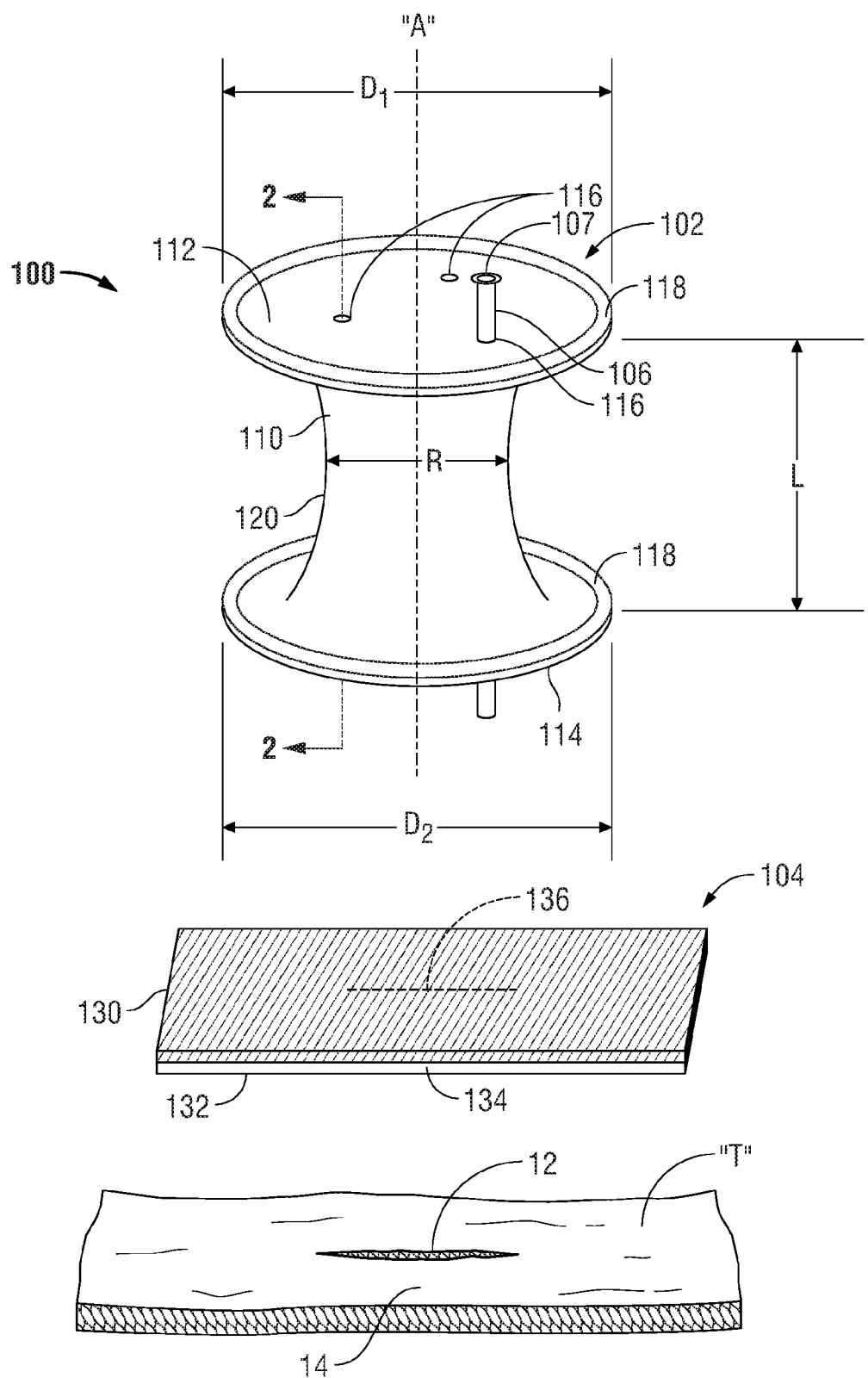
FIG. 1 is a front perspective view of a surgical access system including a portal member and a patch positioned relative to tissue in accordance with the principles of the present disclosure.

In accordance with the present disclosure, a surgical access system is utilized to access a surgical site. The surgical access system includes a surgical portal apparatus, e.g., a portal member, adapted for insertion into an opening, e.g., an incision, in tissue to form a fluid-tight seal with the tissue and an adhesive patch that creates an artificial surface or interface through which the portal member may be placed.

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to a clinician and the term "distal" or "leading" refers to the end of the apparatus that is farther from a clinician. As used herein, the term "patient" should be understood as referring to a human subject or other animal, and the term "clinician" should be understood as referring to a doctor, nurse, or other care provider and may include support personnel. In the following description, well-known functions or constructions are not described in detail to avoid obscuring the present disclosure in unnecessary detail.

One type of minimal invasive surgery described herein is multiple instrument access through a single surgical port. Multiple instrument access through a single surgical port is a minimally invasive surgical procedure, which permits a clinician to operate through a single entry point, typically the patient's navel. The disclosed multiple instrument access through a single surgical port procedure may involve insufflating the body cavity and positioning a portal member within, e.g., the navel of the patient. Examples of surgical instruments or objects which may be introduced through the portal member include clip appliers, graspers, dissectors, retractors, staplers, forceps, laser probes, photographic devices, trocars, cannulas, endoscopes, laparoscopes, arthroscopes, tubes, electrosurgical cutting, coagulating, and ablation devices, and other tools within the purview of those skilled in the art.

Referring now to the drawings, in which like reference numerals identify identical or substantially similar parts throughout the several views, FIG. 1 illustrates a surgical access assembly 100 including a portal member 102 and a patch 104 that may be used in any endoscopic, laparoscopic, and/or open surgical procedure in accordance with the principles of the present disclosure. Portal member 102 includes an elongated body 110 defining a longitudinal axis "A" and including trailing (or proximal) and leading (or distal) ends 112 and 114, respectively. Portal member 102 includes at least one longitudinal port 116, in embodiments, a plurality of longitudinal ports 116, extending along axis "A" between trailing and leading ends 112 and 114, respectively, and through the elongated body 110. At least one or more ports 116 are dimensioned to receive a surgical object, such as a cannula 106 therethrough. Upon introduction through a respective port 116, the inner surface portions 117 (FIG. 2) defining the port 116 establish and maintain a substantially sealed relation about the surgical object. Cannula 106 may be inserted through the at least one longitudinal port 116 and provides a fluid-tight seal with the port 116. Cannula 106 provides an access port 107 including a valve (not shown) for passage of surgical instruments, e.g., endoscopic instruments, therethrough.

Trailing and leading ends 112 and 114 may define flange segments 118, which may be integrally formed with portal member 102. Trailing end 112 of portal member 102 defines a first diameter $D_1$ and leading end 114 defines a second diameter $D_2$. In embodiments, the respective first and second diameters $D_1$, $D_2$ of the trailing and leading ends 112 and 114 are substantially equivalent, as seen in FIG. 1. In other embodiments, diameters $D_1$, $D_2$ may be different. As depicted in FIG. 1, trailing and leading ends 112 and 114 define substantially planar surfaces. However, it is also contemplated that either or both of trailing and leading ends 112 and 114, respectively, may define surfaces that are substantially arcuate to assist in the insertion of portal member 102 within a tissue opening 12 defined by tissue surfaces 14 and formed in tissue "T", e.g. an incision.

Elongated body 110 defines a radial dimension "R" and extends longitudinally between trailing and leading ends 112 and 114, respectively, to define an axial dimension or length "L". The radial dimension "R" of elongated body 110 varies along the axial dimension, or length, "L" thereof to aid in anchoring portal member 102 within tissue "T". Other embodiments in which the radial dimension "R" remains substantially uniform along the axial dimension "L" thereof is also within the scope of the present disclosure.

The radial dimension "R" of elongated body 110 may be appreciably less than the respective diameters $D_1$, $D_2$ of trailing and leading ends 112 and 114 such that the portal member 102 defines an "hour-glass" shape or configuration to assist in anchoring portal member 102 within tissue "T". However, in alternate embodiments, the radial dimension "R" of elongated body 110 may be substantially equivalent to the respective diameters $D_1$ and/or $D_2$ of trailing and leading ends 112 and 114. In cross section, elongated body 110 may exhibit any suitable configuration, e.g. substantially circular, oval, or oblong.

Portal member 102 may be made from a disposable, compressible, and/or flexible type material, such as, for example, a suitable foam or gel material having sufficient compliance to deform and establish a seal about one or more surgical objects, and also establish a sealing relation with the tissue. The compressible material may be sufficiently compliant to accommodate off axis motion of the surgical object. In one embodiment, the material is a foam including a polyisoprene material. In embodiments, the material may be fabricated from an elastomer such as a soft urethane gel, silicone gel, thermoplastic elastomer, or the like.

Portal member 102 is adapted for insertion within a tissue tract "T", e.g., through the abdominal or peritoneal lining in connection with a laparoscopic surgical procedure. Portal member 102, however, is adapted for insertion within any opening in a patient's skin, e.g., an incision or any naturally occurring orifice. The presently disclosed portal member 102 and surgical access system 100 may be used with a surgically created incision, a naturally occurring opening, or in non-laparoscopic procedures.

When inserted within an opening 12 in tissue "T", portal member 102 is adapted to establish a substantial seal within the opening 12, i.e., with the tissue surfaces 14 defining the opening 12. Portal member 102 is dimensioned to provide a fluid tight seal with an opening 12 of about 2 mm to about 18 mm. In embodiments, portal member 102 is about 5 mm to about 20 mm in diameter in its unbiased, expanded condition. During insertion, portal member 102 may be compressed from its first, expanded condition to a second, compressed condition to permit at least partial passage through the opening 12 in tissue "T". Once within the opening 12, portal member 102 will return toward the first, expanded condition with the outer wall 120 of the portal member 102 establishing a seal with the tissue "T" defining the opening 12.

Portal member 102 may include an insufflation conduit (not shown) mounted within one of ports 116 and connectable to a source of insufflation gases to permit passage of gases, e.g., $CO_2$, to maintain the pneumoperitoneum. Other suitable portal members which may be utilized with the surgical access system 100 of the present disclosure including, for example, those disclosed in commonly assigned U.S. Patent Application Pub. No. 2009/0093752, entitled "Seal Anchor for Use in Surgical Procedures", the entire contents of which is hereby incorporated by reference herein.

Patch 104 includes a non-porous substrate 130 including a tissue facing surface 132 including an adhesive 134 that is adapted to adhere to tissue "T". Non-porous substrate 130 of patch 104 may be a film, foam, mesh, fibrous sheet, or composite thereof adapted to adhere and seal tissue.

Non-porous substrate 130 is fabricated from suitable materials such that the patch 104 has sufficient tensile strength to support the portal member 102 during use in a surgical procedure; is sufficiently inert to avoid foreign body reactions when retained on tissue "T" for long periods of time; and is easily sterilized to prevent the introduction of infection when the patch 104 is placed against opening 112 of tissue "T".

Examples of suitable materials include, for example, polyolefins such as polyethylene (including ultra high molecular weight polyethylene) and polypropylene including atactic, isotactic, syndiotactic, and blends thereof; polyethylene glycols; polyethylene oxides; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; ethylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof.

Patch 104 is dimensioned to surround opening 12 in tissue "T" such that the patch 104 adheres to the surrounding tissue "T" to create a seal around opening 12. Accordingly, patch 104 may be any suitable shape or size, such as rectangular as illustrated in FIG. 1, circular as illustrated in FIG. 3A, among other shapes within the purview of those skilled in the art. In embodiments, patch 104 may be cut to a desired size and shape. Patch 104 may also be substantially planar (FIG. 1) or concave (FIG. 4A) to seal opening 12 of tissue "T".

Adhesive 134 may be applied to a portion of the patch 104, such as coated on the entire tissue facing surface 132 of patch 104 (FIG. 1), or around a periphery thereof (FIG. 4A). It is envisioned that the adhesive may be applied in a random or systematic pattern around the tissue facing surface 132 of patch 104. In embodiments, adhesive 134 is pre-applied to patch 104, while in other embodiments, adhesive 134 may be applied to patch 104 prior to application to tissue "T". Additionally, or alternatively, the patch 104 may include mechanical means for binding to tissue. In embodiments, the patch may include mechanical grips or hooks to achieve, or enhance, adhesivity to tissue.

The adhesive is a biocompatible material capable of effecting temporary attachment between the patch and tissue. Adhesives which may be utilized with the surgical access system of the present disclosure include, but are not limited to, adhesive which cure upon tissue contact, which cure upon exposure to ultraviolet (UV) light, which are two-part systems which are kept isolated from one another and cure upon coming into contact with one another, which are pressure sensitive, which are any combinations thereof, or any other known suitable adhesive. Examples of adhesives include, for example, silicones, acrylics, polyurethanes, polyesters, polyamides, and rubber-based adhesives. In embodiments, a hydrogel is utilized as an adhesive. Hydrogels are materials that absorb solvents (such as water), undergo rapid swelling without discernible dissolution, and maintain three-dimensional networks capable of reversible deformation. Hydrogels may also be utilized as a two-part adhesive system in which the hydrogel is a network of crosslinked molecules formed by reacting first and second hydrogel precursors. The first and second hydrogel precursors include functional groups, e.g., nucleophilic or electrophilic functional groups, which combine to form a cross-linked polymeric product as a result of electrophilic-nucleophilic reactions. Hydrogels include, for example, those using synthetic precursors within the purview of those skilled in the art, such as those used in commercially available products such as FocalSeal® from Genzyme, Inc., Coseal® from Angiotech Pharmaceuticals, and DuraSeal® from Confluent Surgical, Inc. Other examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively.

The adhesive patch facilitates insertion of the portal member within a tissue opening when the opening is an irregular shape or too large to solely accommodate the portal member in sealing relation, e.g., in an incision larger than about 20 mm, for example, larger than about 25 mm to about 30 mm. As illustrated in FIG. 1, an aperture 136 (shown in phantom) may be cut by a clinician into patch 104 to a desired size and shape. Aperture 136 is cut into patch 104 by creating a slit in the non-porous substrate 130 or cutting a desired shape corresponding to the shape of the portal member 102, for example.

Alternatively, the patch may include a pre-formed or pre-patterned aperture. In one embodiment, such as shown in FIG. 3A, patch 204 includes a pre-formed aperture 236. The diameter of aperture 136, 236 should be substantially equal or smaller than the diameter of elongated body 110 of portal member 102 such that a fluid-tight fit is formed between the portal member 102, patch 104, 204, and tissue "T". In another embodiment, as illustrated in FIG. 3B, patch 204 may include one or more pre-patterned apertures 236', 236", and 236'" designated by perforation lines 237', 237", and 237'", respectively, extending around the perimeter of apertures 236', 236", and 236'". The strength of the patch 204 is reduced at each perforation line 237', 237", and 237'" so that the material within the perforation lines 237', 237", and/or 237'" may be pressed, torn, or otherwise removed to form the aperture 236', 236", or 236'". In this manner, the appropriate size of the aperture may be selected at the time of use, corresponding to the size of the portal member. In embodiments, the inner, first perforation line 237' may be configured to tear when a relatively low force is applied to the patch 204 in the vicinity of the perforation line 237', while the second perforation line 237" may tear when a higher lever of force is applied to the patch 204, and the third perforation line 237'" may tear when an even higher level of force is applied to the patch 204 to minimize inadvertent separation at the perforation lines.

In embodiments, as illustrated in FIGS. 4A-4C, non-porous substrate 230 of patch 204 may include a reinforcement member 238, 239, and 240, respectively, to provide the desired strength to the patch 104, to prevent the aperture 236 from expanding, and to support the portal member 102 (FIG. 1) during use. Non-limiting examples of the reinforcement member includes meshes, monofilaments, multifilament braids, staple fibers, and combinations thereof. In embodiments, the reinforcement member 238 may be an additional woven or non-woven structure disposed within at least a portion, or entirely through, the non-porous layer 230 as illustrated in FIG. 4A, or the reinforcement member 239 may be positioned on a surface of the non-porous layer 230, as illustrated in FIG. 4B, to form a multi-layered structure. In some embodiments, patch 204 may be reinforced by stitching the periphery of aperture 236 with a monofilament or multifilament thread 240, e.g., a suture, as illustrated in FIG. 4C.

In use, the operator of the surgical access system 100 will insert the portal member 102 into the opening 12 of tissue "T" such that portal 102 is disposed within opening 12. Flanges 118 of the portal member 102 may aid in anchoring the portal member 102 in tissue "T". Surgical instruments, such as a cannula, may then be inserted into longitudinal port 116 of portal member 102 and procedures, e.g., minimally invasive procedures, may be performed. To remove or pass a specimen through the tissue "T" (e.g., the permanent removal of diseased internal anatomy and/or temporary removal of portions of the colon to be manipulated outside of the body before being returned to inside the body), the portal member 102 is removed and the opening 12 is enlarged to allow for passage of the specimen therethrough. Thereafter, patch 104 may be applied to the enlarged opening 12 and portal member 102 may be inserted therethrough so that the procedure proceeds in a manner described above without requiring multiple incisions for accessing the surgical site.

It should be understood that the surgical access system 100 may also be used where a relatively large opening exists that is too large to accommodate a portal member.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the system based on the above-described embodiments. Accordingly, the present disclosure is not to be limited by what has been particularly shown and described, except as indicated by the appended claims.

What is claimed is:

1. A surgical access system comprising:
    a portal member defining a longitudinal axis and including at least one port configured for passage of a surgical object, the portal member comprising a material adapted to be received in sealing relation with an opening in tissue upon insertion of the portal member through the opening; and
    a patch including a substrate having a tissue facing surface and an adhesive supported on the tissue facing surface, the patch being configured to be positioned over the opening in the tissue, the patch defining an aperture dimensioned for sealed reception of the portal member.

2. The surgical access system of claim 1, wherein the material is compressible and is adapted to transition from a first expanded condition to a second compressed condition such that the outer surface of the portal member is in sealing relation with tissue defining the opening.

3. The surgical access system of claim 1, wherein the at least one port is parallel to the longitudinal axis.

4. The surgical access system of claim 1, wherein the aperture is pre-formed in the patch.

5. The surgical access system of claim 1, wherein the patch includes a plurality of pre-patterned apertures defined by perforation lines.

6. The surgical access system of claim 1, wherein the patch is planar.

7. The surgical access system of claim 1, wherein the patch is concave.

8. The surgical access system of claim 1, wherein the adhesive is positioned to entirely coat the tissue facing surface of the substrate.

9. The surgical access system of claim 1, wherein the adhesive is positioned to coat a peripheral portion of the tissue facing surface of the substrate.

10. The surgical access system of claim 1, wherein the patch includes a reinforcement member.

11. The surgical access system of claim 10, wherein the reinforcement member is selected from the group consisting of meshes, monofilaments, multifilament braids, staple fibers, and combinations thereof.

12. The surgical access system of claim 10, wherein the reinforcement member is disposed within the patch.

13. The surgical access system of claim 10, wherein the reinforcement member is disposed on a surface of the patch.

14. The surgical access system of claim 1, wherein the portal member defines leading and trailing ends, the at least one port extending between the leading and trailing ends and being adapted to receive a surgical object whereby the material defining the at least one port is adapted to deform to sealingly engage the surgical object positioned within the port.

15. The surgical access system of claim 1, further comprising a cannula positioned through the at least one longitudinal port for accessing a surgical site.

16. The surgical access system of claim 1, wherein the substrate is non-porous.

* * * * *